United States Patent
Chuter

(10) Patent No.: US 10,406,330 B2
(45) Date of Patent: Sep. 10, 2019

(54) BALLOON CATHETERS

(71) Applicant: Timothy A. M. Chuter, San Francisco, CA (US)

(72) Inventor: Timothy A. M. Chuter, San Francisco, CA (US)

(*) Notice: Subject to any disclaimer, the term of this patent is extended or adjusted under 35 U.S.C. 154(b) by 7 days.

(21) Appl. No.: 14/757,960

(22) Filed: Dec. 24, 2015

(65) Prior Publication Data

US 2016/0193455 A1 Jul. 7, 2016

Related U.S. Application Data

(60) Provisional application No. 62/096,844, filed on Dec. 24, 2014.

(51) Int. Cl.
*A61M 25/10* (2013.01)

(52) U.S. Cl.
CPC .. *A61M 25/10184* (2013.11); *A61M 25/1002* (2013.01); *A61M 25/1029* (2013.01)

(58) Field of Classification Search
CPC ........ A61M 25/10184; A61M 25/1029; A61M 25/1006; A61M 25/1009; A61M 2025/1075
See application file for complete search history.

(56) References Cited

U.S. PATENT DOCUMENTS

| | | |
|---|---|---|
| 5,112,304 A | 5/1992 | Barlow et al. |
| 5,378,237 A | 1/1995 | Boussignac et al. |
| 5,779,685 A | 7/1998 | Thompson et al. |
| 6,712,853 B2 | 3/2004 | Kuslich |
| 6,776,772 B1 | 8/2004 | Vrijer et al. |
| 2005/0271844 A1 | 12/2005 | Mapes et al. |
| 2006/0079836 A1* | 4/2006 | Holman ............... A61M 25/10 604/96.01 |
| 2007/0106216 A1* | 5/2007 | Noddin ............ A61M 25/1029 604/103.09 |

(Continued)

FOREIGN PATENT DOCUMENTS

| | | |
|---|---|---|
| EP | 2077886 A2 | 7/2009 |
| WO | 2007065137 A2 | 6/2007 |

OTHER PUBLICATIONS

European Patent Office, Search Report for corresponding European Application No. 15873823.7-1132, dated Jul. 19, 2018, 7 pages.

(Continued)

*Primary Examiner* — Bhisma Mehta
*Assistant Examiner* — Hamza A Darb
(74) *Attorney, Agent, or Firm* — William A. English; Vista IP Law Group LLP

(57) ABSTRACT

Catheters or other tubular devices and methods for using them to perform a medical procedure are provided. In an exemplary embodiment, a tubular device includes an elongate tubular member comprising a proximal end, a distal end sized for introduction into a patient's body, and a lumen extending between the proximal and distal ends; an expandable member on the distal end comprising an outer impermeable membrane with an inner surface surrounding a substantially enclosed interior space; and a fiber network within the interior space coupled to the inner surface and configured to limit expansion of the membrane when inflation media is directed into the interior space from the lumen to expand the membrane to an expanded configuration.

26 Claims, 4 Drawing Sheets

(56) References Cited

U.S. PATENT DOCUMENTS

2010/0243135 A1* 9/2010 Pepper ................. A61M 25/10
156/189
2010/0318029 A1 12/2010 Pepper et al.

OTHER PUBLICATIONS

Korean Intellectual Property Office, International Search Report for corresponding International Application No. PCT/US2015/000440, Form PCT/ISA/210, dated May 2, 2016, 5 pages.
Korean Intellectual Property Office, Written Opinion for corresponding International Application No. PCT/US2015/000440, Form PCT/ISA/237, dated May 2, 2016, 6 pages.

* cited by examiner

BALLOON CATHETERS

RELATED APPLICATION DATA

The present application claims benefit of provisional application Ser. No. 62/096,844, filed Dec. 24, 2014, the entire disclosure of which is expressly incorporated by reference herein.

FIELD OF THE INVENTION

The present invention relates to catheters and to methods for making and using catheters. More particularly, the present invention relates to catheters including balloons with internal supports and/or that otherwise expand to non-circular profiles, and to methods for making and using catheters including such balloons.

BACKGROUND

Balloons are good at providing substantially uniform forces to the walls of a body lumen because most such lumens have a circular cross-sectional profile, as do most balloons. Indeed, it is difficult to create a balloon that, upon inflation, assumes other shapes other than cylindrical shapes with circular cross-sectional profiles since such a shape generally minimizes wall tension by maximizing the ratio of volume to surface area.

A balloon's tendency to adopt a circular profile becomes a problem when the balloon is being used to apply force to a non-circular surface. Pressure is applied uniformly only when the shape of the impacted surface matches the shape of the balloon (i.e., circular). Many compressive applications, outside the bounds of a body lumen, call for balloons of fixed, non-circular, inflated shape.

Accordingly, balloons that may be expanded to non-circular profiles would be useful.

SUMMARY

The present invention is directed to catheters and to methods for making and using catheters. More particularly, the present invention is directed to catheters including balloons with internal supports and/or that otherwise expand to non-circular profiles, and to methods for making and using catheters including such balloons.

There are several ways to impose a non-circular profile on an inflated balloon by placing rigid elements in its wall, but these elements are not easily compressed into a low-profile configuration for atraumatic insertion.

An alternative approach employs multiple balloons, each of which assumes a circular cross-sectional profile when inflated, while the combined multi-balloon structure may have a different shape. However, the surface of the balloon will inevitably have a bumpy surface reflecting the curvature of individual balloons. Increasing the number of constituent balloons reduces the bumpiness, but increases the bulk.

Besides, the walls of all of the internal balloons serve only to constrain the outward movement of the balloons in the surface layer: a function that can be performed equally well by an internal network of fibers. The network of fibers can take many forms, since it serves only to resist the outward expansion of the balloon envelope. If the fibers are substantially inelastic and interconnected, the maximally expanded shape of the fiber mass becomes the maximally expanded shape of the balloon envelope that is securely glued to its outer surface. In an exemplary embodiment, the fiber mass may resemble a sponge, or a scrubbing pad, made of interconnected strands of flexible polymer or flexible metal wire.

In accordance with an exemplary embodiment, a tubular device is provided for performing a medical procedure that includes an elongate tubular member comprising a proximal end, a distal end sized for introduction into a patient's body, and a lumen extending between the proximal and distal ends; an expandable member on the distal end comprising an outer impermeable membrane with an inner surface surrounding a substantially enclosed interior space; and a fiber network within the interior space coupled to the inner surface and configured to limit expansion of the membrane when inflation media is directed into the interior space from the lumen to expand the membrane to an expanded configuration.

In accordance with another embodiment, a method is provided for performing a medical procedure within a patient's body that includes providing an expandable member on a distal end of a tubular device, the expandable member comprising an outer membrane with an inner surface surrounding a substantially enclosed interior space and a fiber network within the interior space coupled to the inner surface; compressing the expandable member to a compressed configuration; introducing the distal end with the expandable member in the compressed configuration into a patient's body; positioning the expandable member adjacent a body structure within the patient's body; and expanding the expandable member to an expanded configuration to contact the body structure, the fiber network limiting expansion of the membrane.

Other aspects and features including the need for and use of the present invention will become apparent from consideration of the following description taken in conjunction with the accompanying drawings.

BRIEF DESCRIPTION OF THE DRAWINGS

It will be appreciated that the exemplary apparatus shown in the drawings are not necessarily drawn to scale, with emphasis instead being placed on illustrating the various aspects and features of the illustrated embodiments. The drawings illustrate exemplary embodiments, in which.

DETAILED DESCRIPTION OF THE EXEMPLARY EMBODIMENTS

Figure 1:
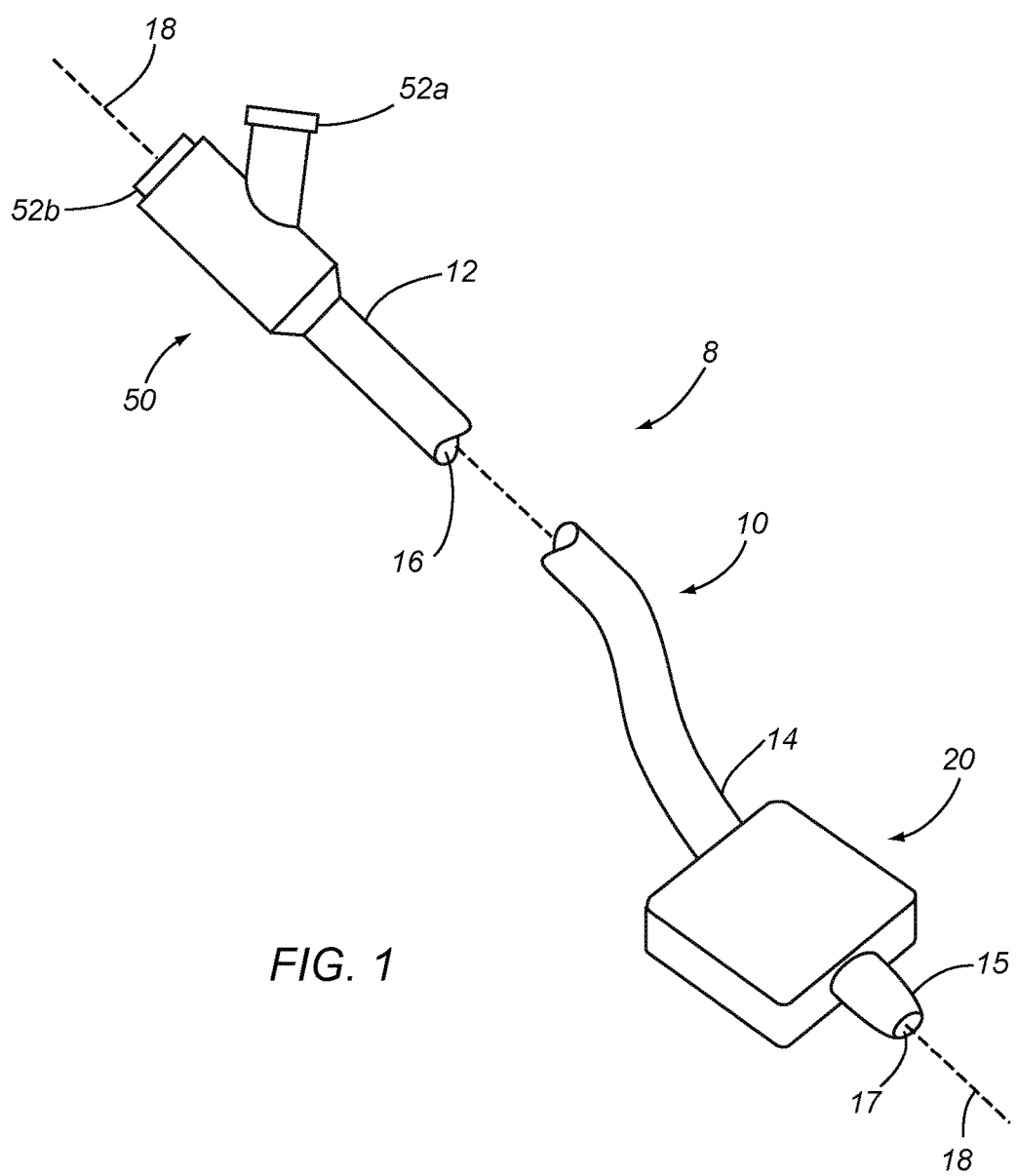
FIG. 1 is a perspective view of an exemplary embodiment of a catheter including a non-circular balloon carried on its distal end.

Turning to the drawings, FIG. 1 shows an exemplary embodiment of a catheter 8 including a tubular member or body 10 and a balloon 20 carried thereon. As described further elsewhere herein, the balloon 20 generally includes an internal network of fibers 30 (e.g., as shown in FIGS. 2A-2D) that limit expansion of the balloon 20 in a predetermined manner, e.g., to cause the balloon 20 to expand into a non-circular or non-cylindrical shape, such as a rectangular or other shape defining one or more substantially planar walls.

Generally, the tubular member 10 includes a includes a proximal end 12, e.g., including a handle or hub 50, a distal end 14 sized and/or shaped for introduction into a patient's body, and one or more lumens 16 extending therebetween, thereby generally defining a longitudinal axis 18. For example, an inflation lumen 16a may be provided that extends from a side port 52a on the hub 50 to communicate between a source of inflation media, e.g., a syringe (filled with inflation gas or fluid, such as saline, not shown) and an interior of the balloon 20. Optionally, one or more additional lumens may be provided, e.g., a guidewire or instrument lumen extending between a port 52b on the proximal end and an outlet 17 on the distal end 14 (not shown).

In one embodiment the catheter 8 may have a substantially homogenous construction between the proximal and distal ends 12, 14. Alternatively, the construction may vary along the length of the catheter 8 to provide desired properties. For example, a proximal portion of the tubular member 10 adjacent the proximal end 12 may be substantially rigid or semi-rigid, e.g., providing sufficient column strength to allow the distal end 14 of the catheter 8 to be pushed or otherwise manipulated from the proximal end 12, while the distal portion 24 may be substantially flexible.

As shown in FIG. 1, the balloon 20 may be mounted around the distal end 14, e.g., such that the tubular member 10 terminates in a tapered and/or otherwise atraumatic distal tip 15. Alternatively, the balloon 20 may be mounted to the distal tip such that the balloon 20 extends partially or entirely distally beyond the distal end 14, e.g., similar to the embodiment shown in FIGS. 2A-2D.

Figure 2A:
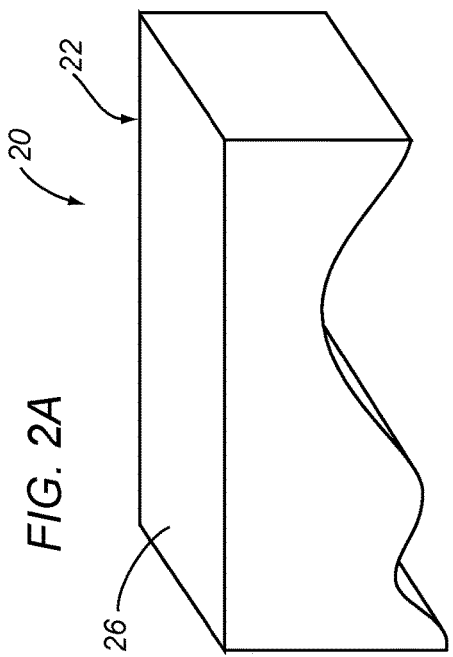
FIGS. 2A and 2B are perspective and cross-sectional views, respectively, of an exemplary embodiment of a non-circular balloon, including an internal fiber network in an expanded configuration, which may be provided on the catheter of FIG. 1.
Figure 2B:
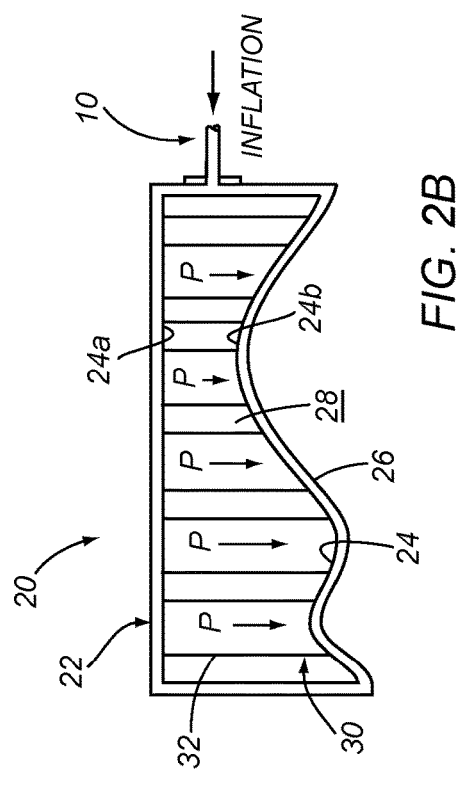
Figure 2C:
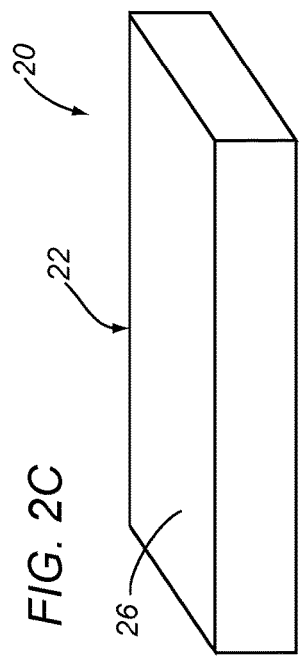
FIGS. 2C and 2D are perspective and cross-sectional views, respectively, of the balloon of FIGS. 2A and 2B in a compressed configuration.
Figure 2D:
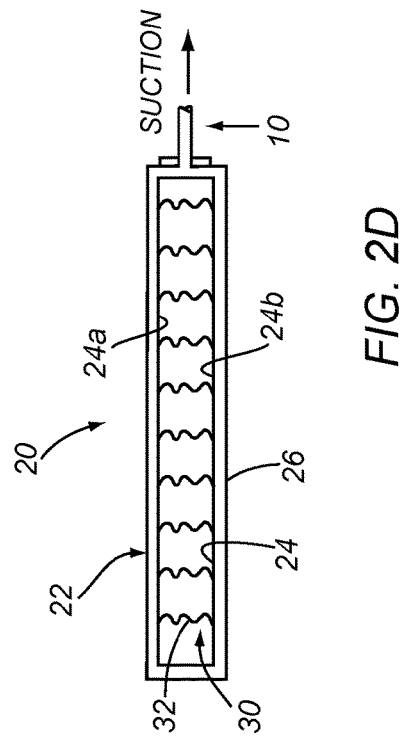

FIGS. 2A-2D show an exemplary embodiment of a balloon 20 that includes an outer balloon membrane 22 and an internal supporting structure, e.g., a fiber network 30 including a plurality of fibers 32. The membrane 22 generally includes inner surfaces 24 and outer surfaces 26 and defines a substantially enclosed interior space 28. Generally, the balloon 20 is expandable between a compressed or delivery configuration (e.g., as shown in FIGS. 2C and 2D), and an expanded configuration (e.g., as shown in FIGS. 2A and 2B).

The fiber network 30 is configured to limit expansion and/or deformation of the membrane 22, e.g., to configure the balloon 20 in a predetermined shape when expanded. For example, fibers 32 may be formed from substantially inelastic materials and their lengths may be set to subject the fibers 32 to tension when the balloon is expanded to the expanded configuration. The fiber network 30 may limit balloon expansion most in any direction that is substantially parallel to the preponderant direction of the fibers 32.

For example, as shown in FIG. 2B, the fibers 32 extend from a first inner surface 24a across the interior space 28 to a second opposite inner surface 24b. In this manner, the fiber network 30 may be configured to limit expansion of the balloon 20 in a single direction, e.g., along a longitudinal axis of the fibers 32 when the balloon 20 is expanded and the fibers 32 are subjected to tensile load, as can be seen in FIGS. 1A and 1B.

Figure 3A:
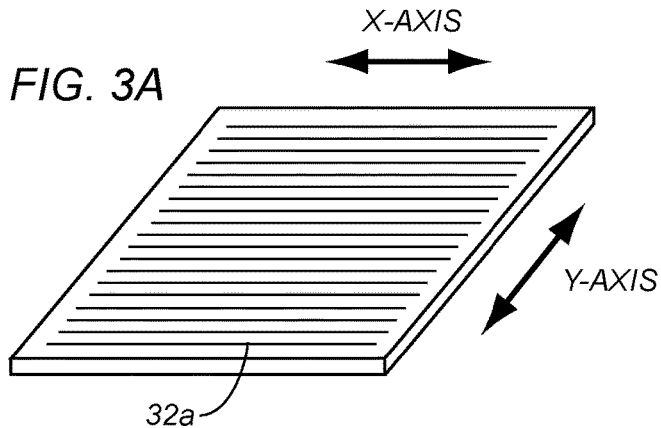
FIGS. 3A-3C are perspective views of exemplary configurations of fiber networks that may be included within a balloon, such as the balloon shown in FIGS. 2A-2D.
Figure 3B:
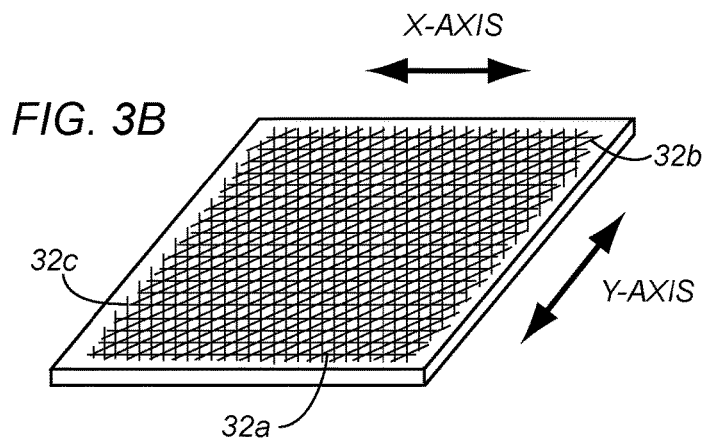
Figure 3C:
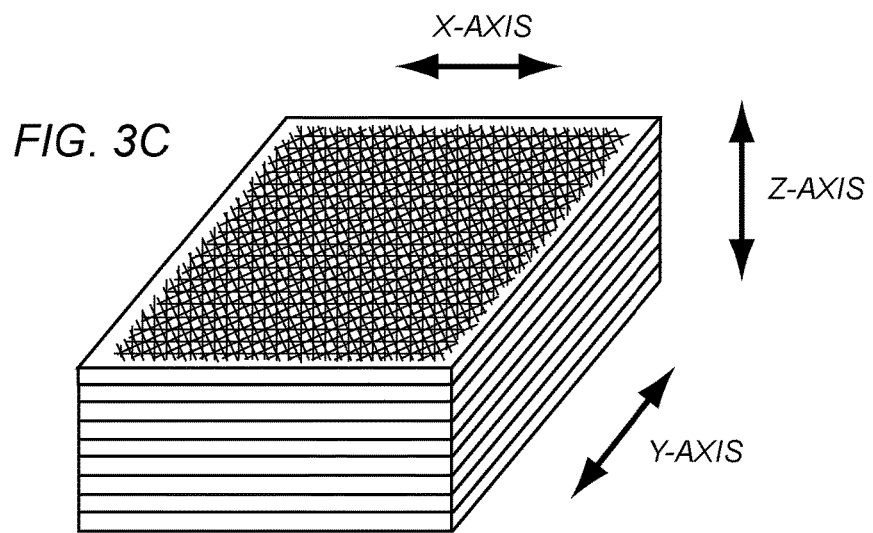

Optionally, the fiber network 30 may include multiple sets of fibers (not shown) that limit expansion of the balloon 20 in multiple directions, e.g., as illustrated in FIGS. 3A-3C.

As shown in FIG. 3A, if there is only one layer and all the fibers 32a of that layer run in the same direction (e.g., along an x-axis), expansion is most limited in the direction of the fibers (along the x-axis). If, as shown in FIG. 3B, the fibers 32a, 32b, 32c within a particular layer run in multiple directions (e.g., along the x-axis, y-axis, or both axes), expansion is limited in all directions lying within the plane of that layer. Further, as shown in FIG. 3C, a multiple-layer fiber network may impose stricter limitations on the shape and dimensions of the expanded balloon within a plane parallel to the layers (along the x-axis and y-axis) than in the direction perpendicular to the layers (along the z-axis). The in-plane expansion of a layered multi-direction (x-axis, y-axis, and z-axis) fiber network depends largely on the elasticity of the fibers, whereas z-axis expansion depends on the elasticity, stiffness and inter-connection distance.

The membrane 30 may be formed from substantially elastic or other impermeable material depending on whether the balloon 20 is intended to be compliant or semi-compliant, and/or depending on the intended shape and pressure requirements. The overall shape of the balloon 20 may be configured based on the corresponding shape of a body structure being compressed and/or otherwise engaged by the balloon 20. For example, the balloon 20 may be configured to provide a compression surface 26b in the expanded configuration similar to a body structure to be compressed during a medical procedure.

Returning to FIGS. 2A-2D, a rectangular balloon 20 is shown that includes a membrane 22 that includes a layer of adhesive on the inner surface 24, and a rectangular mass of fibers 32 providing the fiber network 30. In addition, the balloon 20 includes an inflation port 40 communicating with the interior space 28 to direct the balloon 20 between the compressed configuration shown in FIGS. 2C and 2D and the expanded configuration shown in FIGS. 2A and 2B, thereby providing the compression surface 26b. Upon inflation, the internal pressure is distributed evenly through the compression surface, despite the irregularity of the body structure being compressed.

The balloon 20 may be collapsed to the compressed configuration through the combined effects of compression and suction. For example, a source of vacuum, e.g., a syringe, suction line, and the like (not shown), may be coupled to the inflation port 40 (e.g., via the side port 52a shown in FIG. 1) and fluid aspirated from the interior space 28, thereby causing the membrane 22 to collapse inwardly and compress or collapse the fibers 32 of the fiber network 30. For example, if the fibers 32 are substantially inelastic yet flexible, the fibers 32 may simply relax when tension is removed as the membrane 22 is drawn inwardly or if a multiple dimensional network is provided, the fibers may compress inwardly, similar to a sponge compressing.

Conversely, when the balloon 20 is to be expanded, a source of inflation media, e.g., the same syringe, a fluid line, and the like (not shown), may be coupled to the inflation port 40 and fluid may be delivered into the interior space 28 to expand the membrane 22. When the membrane 22 expands sufficiently, the fibers 32 may be subjected to tensile forces, e.g., thereby preventing further expansion of the membrane 22 if the fibers are substantially inelastic.

To make the balloon 20, the fibers 32 of the fiber network may be bonded or otherwise attached to the inner surface 24 of the membrane 22. In one embodiment, a layer of adhesive (not shown) may be applied to the inner surface 24 and ends of the fibers 32 may be attached to the inner surface 24 such that the fibers 32 extend across the interior space 28 in a desired manner. For example, opposites ends of the fibers 32 may be attached to different locations of the inner surface 24, e.g., generally opposite one another or otherwise to orient the fibers along a desired axis.

Alternatively, the fibers 32 may be bonded or otherwise coupled together to provide a mass of fibers that are then inserted into the interior space 28 of the membrane 20 and bonded collectively to the inner surface 24. In a further alternative, the fibers 32 may be attached together within a porous material, e.g., a fabric and the like (not shown), to create an encased fiber network 30, with the porous material providing an outer surface for the fiber network 30 that may be attached to the inner surface 24 of the membrane 20.

In a further alternative, the interior space 28 of the balloon 20 may be substantially filled with a sponge or other similar filler material having a predetermined relaxed shape corresponding to the desired outer dimension of the balloon 20, yet resiliently compressible inwardly similar to the fiber network described herein. For example, the filler material may be formed from substantially inelastic material that prevents expansion beyond the relaxed shape, yet allows the filler material to be compressed inwardly. In this alternative, an outer surface of the filler material may be attached to the inner surface of the membrane 22 to prevent separation of the membrane from the filler material. Thus, expansion of the membrane 22 may be limited by the predetermined relaxed shape of the filler material.

The resulting balloon 20 may be attached to a catheter or other tubular member, such as the catheter 8 shown in FIG. 1, to allow introduction into a patient's body. For example, the balloon 20 may be attached to the distal end 14 of the tubular member 10, e.g., such that the distal end 14 of the catheter 8 terminates on one end of the balloon 20, e.g., providing the inflation port 40 shown in FIGS. 2A-2D.

Alternatively, the distal end 14 of the tubular member 10 may extend through the balloon 20, e.g., as shown in FIG. 1. For example, the membrane 22 may include proximal and distal ends that are attached to the catheter distal end 14 such that the ends are spaced apart from one another. In this alternative, the fiber network 30 may be located within the interior space 28 of the membrane 22 surrounding the catheter distal end 14. Optionally, the fibers of the fiber network 30 may be coupled to the wall of the catheter distal end 14 in addition to the inner surface 24 of the membrane 22.

In another alternative, the distal end 14 of the tubular member 10 may be coupled to the proximal end of the membrane 22 and a separate tip member (not shown) may be coupled to and extend from the distal end of the membrane 22.

To make the balloon 20, one or more sections of membrane material may be formed to define one or more sidewalls of the membrane 22, e.g., by molding as a single piece, forming multiple sheets and then attaching them together, e.g., by bonding with adhesive, sonic welding, fusing, and the like. The fiber network 30 may be placed within the interior 28 of the membrane 22 after forming one or more of the sidewalls, e.g., by omitting one of the end walls and otherwise forming the rest of the membrane 22 to allow access to the interior space 28. A layer of adhesive may be applied to one or more interior surfaces of the membrane 22, e.g., opposite sidewalls, and the fiber network 30 may be positioned within the interior space 28 such that ends of the fibers 32 become bonded to the interior surfaces via the adhesive. In one embodiment, individual fibers 32 may be positioned and bonded to the interior surfaces. In another embodiment, multiple fibers 32 may be assembled together, e.g., as shown in FIGS. 3A-3C, and inserted together into the interior space 28 such that the ends are bonded to the desired interior surfaces. Any remaining sidewalls may then be attached to form the complete membrane 22. In an alternative embodiment, the fiber network 30 may be positioned within the interior space 28 when the membrane 20 is initially formed, e.g., by placing the fiber network 30 within a mold into which membrane material is delivered to form the membrane 22 directly around the fiber network 30. In another alternative, after forming the membrane 20, the interior space 28 may be accessed through an opening in one of the sidewalls, e.g., a neck or other opening used to connect the membrane 20 to the distal end 14 of the tubular member 10.

During use, the balloon 20 may be introduced into a patient's body in the compressed configuration and positioned at a desired location, e.g., aligning one or more sidewalls of the balloon 20 with a correspondingly shaped body structure. For example, the distal end 14 may be introduced into a body lumen or cavity, e.g., via an access sheath, guidewire, or other instrument (not shown) previously positioned from an access site into the treatment location. If desired, the distal end 14 may be rotated and/or otherwise manipulated to orient the sidewalls(s) of the balloon 20 towards a body structure at the treatment location. Optionally, the distal 14 and/or balloon 20 may include one or more markers, e.g., radiopaque markers and the like (not shown), to aid in manipulation of the balloon 20 using external imaging, such as fluoroscopy.

Once properly positioned, the balloon 20 may be expanded to the expanded configuration, e.g., to press the sidewall(s) of the balloon 20 against the body structure. In exemplary embodiments, the balloon 20 may be used to apply pressure to the body structure, e.g., with the irregularly shaped sidewall(s) applying a substantively uniform pressure to the similarly shaped surface of the body structure. In addition, the balloon 20 may enhance apposition or contact with the body structure to provide additional treatments, e.g., deliver one or more drugs or agents from the sidewall(s) to the body structure, deliver energy via the balloon 20, and the like. For example, the balloon 20 may carry one or more treatment elements, e.g., coatings, porous members, electrodes, delivery devices, and the like (not shown) that may be used to provide additional treatment.

Providing the internal support structure 30 within a compliant balloon 20 may limit shape and/or size shape of the balloon 20 in the expanded configuration, allowing the balloon 20 to be inflated to relatively high pressures compared to conventional compliant balloons. Without the internal support, high-pressure inflation of a compliant balloon may cause it to expand uncontrollably wherever the body lumen is widest or weakest and/or can risk rupture of the balloon.

Figure 4:
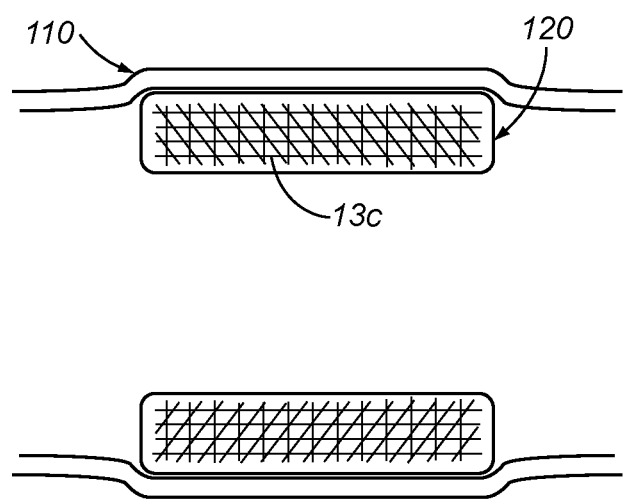
FIG. 4 is a cross-sectional view of an exemplary embodiment of an internally supported balloon supporting a tubular prosthesis.
Figure 5:
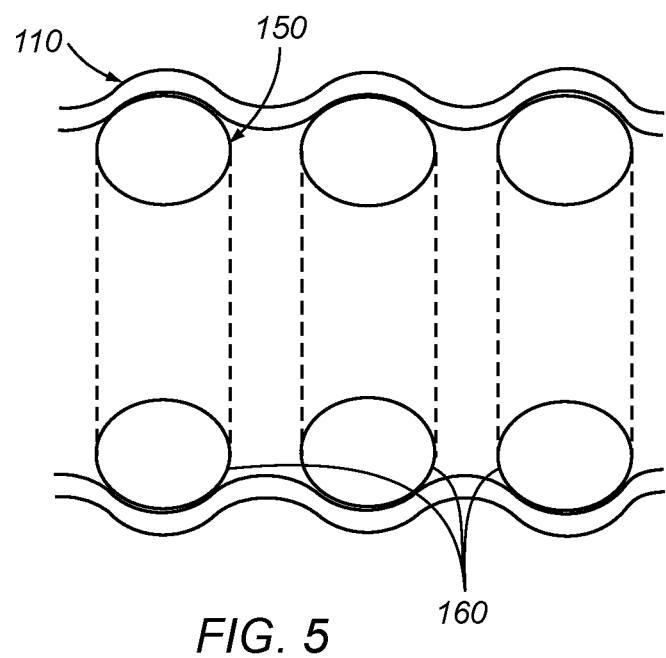
FIG. 5 is a cross-sectional view of a conventional balloon expanded within a tubular prosthesis.

Turning to FIGS. 4 and 5, in another application, the balloons and/or catheters herein may be used to support a tubular graft or stent. FIG. 4 shows an exemplary embodiment of an internally supported balloon 120, which may be constructed similar to any of the embodiments herein, expanded within a tubular prosthesis 110, which may be a stent, stent-graft, or other tubular device configured for implantation within a body lumen.

Several current devices employ inflatable rings or spirals to provide structural support and enhance sealing, e.g., as demonstrated by the balloon 150 shown in FIG. 5 including one or more rings 160. Like all balloons, each ring 160 has a circular cross-sectional profile with a depth (outer wall to inner wall) that matches its length (parallel to the long-axis of the prosthesis). To minimize luminal impingement, the ring 160 has to be relatively narrow.

In contrast, as shown in FIG. 4, the presence of a fiber support structure 130 within the interior of the balloon 120 allows the otherwise circular cross-sectional profile to become rectangular. The resulting supporting annular body may then become longer than it is deep, which maximizes the length of the contact zone while minimizing luminal impingement. Thus, the overall length and thickness of the balloon 120 may be set as desired using the internal supporting structure, e.g., to correspond to the prosthesis 110 being supported.

While the invention is susceptible to various modifications, and alternative forms, specific examples thereof have been shown in the drawings and are herein described in detail. It should be understood that the invention is not to be limited to the particular forms or methods disclosed, but to the contrary, the invention is to cover all modifications, equivalents and alternatives falling within the scope of the appended claims.

I claim:

1. A tubular device for performing a medical procedure, comprising:
   an elongate tubular member comprising a proximal end, a distal end sized for introduction into a patient's body, and a lumen extending between the proximal end and the distal end;
   an expandable member on the distal end comprising an outer impermeable membrane surrounding an enclosed interior space, the membrane comprising an inner first surface and an inner second surface generally opposite the inner first surface; and
   a fiber network within the interior space coupled to the inner first surface and the inner second surface and configured to limit expansion of the membrane when an inflation media is directed into the interior space from the lumen to expand the membrane to an expanded configuration,
   wherein the fiber network comprises a plurality of fibers comprising first ends coupled to the inner first surface and second ends coupled to the inner second surface such that intermediate regions of all of the plurality of fibers extend across the interior space substantially parallel to one another when the membrane is expanded to the expanded configuration to limit expansion of the membrane in a direction along a longitudinal axis of the plurality of fibers.

2. The tubular device of claim 1, wherein the fiber network limits the membrane to adopting a non-circular shape in the expanded configuration.

3. The tubular device of claim 2, wherein a sidewall of the membrane defining one of the inner first surface and the inner second surface of the membrane has a substantially planar surface in the expanded configuration.

4. The tubular device of claim 1, wherein the plurality of fibers are oriented for limiting expansion of one or more sidewalls of the membrane to a substantially planar shape in a direction substantially perpendicular to the longitudinal axis of the plurality of fibers.

5. The tubular device of claim 1, wherein the plurality of fibers are formed from a substantially inelastic material.

6. The tubular device of claim 1, wherein the membrane is formed from an elastic material.

7. The tubular device of claim 1, wherein the membrane is formed from a substantially inelastic material.

8. The tubular device of claim 1, further comprising a source of vacuum coupled to the proximal end and communicating via the lumen with the interior space, the source of vacuum actuatable to apply sufficient vacuum to the interior space and compress the membrane and the fiber network to a compressed configuration for introduction into the patient's body.

9. The tubular device of claim 8, wherein the fiber network is configured to bias the membrane towards the expanded configuration when the vacuum is discontinued.

10. The tubular device of claim 8, further comprising a source of inflation media coupled to the proximal end and communicating via the lumen with the interior space, the source of inflation media actuatable to direct inflation media into the interior space to increase internal pressure and expand the membrane to the expanded configuration.

11. The tubular device of claim 10, wherein the source of vacuum and the source of inflation media are the same device.

12. The tubular device of claim 1, wherein the membrane comprises proximal and distal ends attached to the tubular member distal end such that the membrane proximal and distal ends are spaced apart from one another, and wherein the plurality of fibers are spaced apart within the interior space between the membrane proximal and distal ends.

13. The tubular device of claim 1, wherein the membrane comprises a proximal end and a distal end, and where the distal end of the tubular member is coupled to the membrane proximal end such that the expandable member extends distally beyond the tubular member distal end.

14. A tubular device for performing a medical procedure, comprising:
   an elongate tubular member comprising a proximal end, a distal end sized for introduction into a patient's body, and a lumen extending between the proximal end and the distal end;
   an expandable member comprising first and second opposite ends attached to the distal end comprising an outer impermeable membrane surrounding an enclosed interior space, the membrane comprising an inner first surface and an inner second surface generally opposite the inner first surface; and
   a fiber network within the interior space comprising:
   a first plurality of fibers including first ends coupled to the inner first surface and second ends coupled to the inner second surface such that all of the first plurality of fibers extend across the interior space substantially parallel to one another when the membrane is expanded to an expanded configuration to limit expansion of the membrane in a first direction along a longitudinal axis of the first plurality of fibers, and
   a second plurality of fibers, all of the second plurality of fibers oriented orthogonally relative to the first plurality of fibers and extending across the interior space substantially parallel to one another when the membrane is expanded to the expanded configuration to limit expansion of the membrane in a second direction along a longitudinal axis of the second plurality of fibers such that the membrane defines a plurality of substantially planar walls extending between the first and second ends of the expandable member in the expanded configuration.

15. The tubular device of claim 14, wherein opposite ends of the second plurality of fibers are coupled to an inner third surface and an inner fourth surface of the membrane.

16. The tubular device of claim 15, wherein the second direction is substantially perpendicular to the first direction.

17. A method for performing a medical procedure within a patient's body, comprising:

providing an expandable member on a distal end of a tubular device, the expandable member comprising an outer membrane with an inner surface surrounding an enclosed interior space and a fiber network within the interior space, the fiber network comprising a plurality of fibers comprising first ends coupled to an inner first surface of the membrane and second ends coupled to an inner second surface generally opposite the inner first surface such that intermediate regions of the plurality of fibers extend across the interior space;

compressing the expandable member to a compressed configuration;

introducing the distal end with the expandable member in the compressed configuration into a patient's body;

positioning the expandable member adjacent a body structure within the patient's body; and expanding the expandable member to an expanded configuration to contact the body structure such that all of the plurality of fibers extend across the interior space substantially parallel to one another to limit expansion of the membrane in a direction along a longitudinal axis of the plurality of fibers.

18. The method of claim 17, wherein the fiber network biases the expandable member towards the expanded configuration, and wherein compressing the expandable member to the compressed configuration comprises applying vacuum to the interior space to compress the membrane and the fiber network to the compressed configuration.

19. The method of claim 18, wherein expanding the expandable member to the expanded configuration comprises removing the vacuum such that the fiber network expands the expandable member towards the expanded configuration.

20. The method of claim 17, wherein the plurality of fibers extend substantially parallel to one another when the membrane is expanded towards the expanded configuration, thereby limiting expansion of a sidewall of the membrane to a substantially planar shape that contacts the body structure.

21. A tubular device for performing a medical procedure, comprising:

an elongate tubular member comprising a proximal end, a distal end sized for introduction into a patient's body, and a lumen extending between the proximal and distal ends;

an expandable member comprising first and second opposite ends attached to the distal end and comprising an outer impermeable membrane with an inner surface surrounding a substantially enclosed interior space; and a fiber network within the interior space configured to limit expansion of the membrane when an inflation media is directed into the interior space from the lumen to expand the membrane to an expanded configuration, the fiber network comprising a plurality of fibers comprising opposite ends coupled to the inner surface such that intermediate regions of the plurality of fibers extend across the interior space and the plurality of fibers limit the membrane to adopting a non-cylindrical shape defining one or more substantially planar walls extending between the first and second opposite ends in the expanded configuration.

22. The tubular device of claim 21, wherein the plurality of fibers are configured to limit expansion of the expandable member to a shape defining the one or more of substantially planar walls that comprises a plurality of substantially planar walls extending between the first and second opposite ends of the expandable member.

23. A method for performing a medical procedure within a patient's body, comprising:

providing an expandable member on a distal end of a tubular device, the expandable member comprising first and second opposite ends attached to the distal end, an outer membrane with an inner surface surrounding a substantially enclosed interior space and a fiber network within the interior space, the fiber network comprising a plurality of fibers comprising opposite ends coupled to the inner surface such that intermediate regions of the plurality of fibers extend across the interior space;

compressing the expandable member to a compressed configuration;

introducing the distal end with the expandable member in the compressed configuration into a patient's body;

positioning the expandable member adjacent a body structure within the patient's body; and expanding the expandable member to an expanded configuration to contact the body structure, the fiber network limiting expansion of the membrane such that the expandable member defines one or more substantially planar walls extending between the first and second opposite ends of the expandable member.

24. The method of claim 23, further comprising, before expanding the expandable member, manipulating the distal end to orient a first substantially planar wall of the one or more substantially planar walls towards the body structure.

25. The method of claim 23, wherein expanding the expandable member to the expanded configuration comprises pressing a first substantially planar wall of the one or more substantially planar walls against the body structure, the method further comprising delivering one or more agents from the first wall to the body structure.

26. The method of claim 23, wherein expanding the expandable member to the expanded configuration comprises pressing a first substantially planar wall of the one or more substantially planar walls against the body structure, the method further comprising delivering energy from one or more elements on the first wall to the body structure.

* * * * *